United States Patent [19]
Bonner et al.

[11] Patent Number: 5,747,336
[45] Date of Patent: May 5, 1998

[54] CLONED HUMAN GENES FOR MUSCARINIC ACETYLCHOLINE RECEPTORS AND CELLS LINES EXPRESSING SAME

[75] Inventors: Tom I. Bonner, Chevy Chase; Mark Robert Brann, Bethesda, both of Md.; Noel J. Buckley, London, England

[73] Assignee: The United States of America as represented by the Department of Health and Human Services, Washington, D.C.

[21] Appl. No.: 294,869

[22] Filed: Aug. 29, 1994

Related U.S. Application Data

[63] Continuation of Ser. No. 944,747, Sep. 14, 1992, abandoned, which is a continuation of Ser. No. 581,538, Sep. 12, 1990, abandoned, which is a continuation of Ser. No. 241,971, Sep. 8, 1988, abandoned.

[51] Int. Cl.$^6$ .......................... C12N 15/85; C12N 15/63; C07H 21/04
[52] U.S. Cl. ................. 435/325; 435/69.1; 435/320.1; 536/23.1; 536/23.5; 935/11; 935/70; 935/71
[58] Field of Search .................... 536/23.1, 23.5; 435/69.1, 172.3, 240.2, 320.1, 325; 935/11, 70, 71

[56] References Cited

PUBLICATIONS

Peralta et al. (a), EMBO Journal b(13):3923–9 (1987).
Peralta et al. (b), Science 236:600–605 (1987).
Bonner et al., Science 237:527–532 (1987).
Brann et al., Molecular Pharmacology 32: 450–5 (1987).
Chen et al., Mol. Cell. Biol. 7:2745–52 (1987).
Jones et al., Mol. Pharmacology 34: 421–426 (1988).
Allard et al, Nucleic Acids Research, vol. 15, No. 24 (1987).

*Primary Examiner*—Jasemine C. Chambers
*Assistant Examiner*—Scott D. Priebe
*Attorney, Agent, or Firm*—Fitch, Even, Tabin & Flannery

[57] ABSTRACT

Clones of human genes for a plurality of different muscarinic acetylcholine receptors and stable cell lines homogeneously expressing a specific subtype of the receptors have been prepared. A method for screening muscarinic drugs has been described.

8 Claims, 10 Drawing Sheets

FIG. 1A

```
1441 GGCAGGGGGCTGCATCCTCAGCCCCAGGGCCCTCAGGCCTCAGGCCTCTCACCTGGCTTCCCAGGACCCCTGCCACCTTTCCCAGACTTCGCTATT
1561 CCCAGGCAGGGAGGGGAAACCCGGGGAACTGGTTTTTCTGTTCCCTGCTGGGTGGGAATGCGCTTCACCAGGAAGAAGGCCCCAGGATCCGGGCTTTGGACTCCTTGTTTGCCT
1681 TTAGGCAGGAAGTCAGGAGCCCAGCCAGGCGGGCCAGGAAGGCTTAACATTAAGTATTCCTTGGCCACGGCCCAGATTGCGGTGTGAGATGGTGCCCCCTGGGGGCACAG
1801 CCAGAAACTGAACTGGCCGCTGGAGAGAAAAGCCAGATGACGGAGCTGGGGAATCCCCTGCTTCATAGGCAGAGCCCGCCACCTGGGCCCACCTGTCACATATCGTTCCACA
1921 AATGTCCTCAGAGGGTCCCTAGTGTGGGTCAACTCCAAGCAATGTCCAAGACAATGACACTGGAAGGTCCGGCTTGGCTTGCTAGTCACATATCAAGTCCCGAGGCAGCAAC
2041 AGGACCAGGAGCCAGGTGTCCTGACTGTCCTACAATATCATTTTCTGGGAGTGGAGTCAAGTGTGCCTGCTATCCAGCCGCAAATCCATACCCCCTGCCCAGAGAAGCCTCAGTCCC
2161 TCCCTCCTGGCTCACAGCCACCACCTGGATGGATCTGCCATGCAGATCTAGCCAGGCCTCCCGATCTCCAGGCCCCACCTGCCCCAAATGTTCTTCCTTTCATCCTCAGCAAGTGCTGAGTCTGTGAATA
2281 TCTCCTGTGAGCTCCCCAATCCAACCATGCATGGCCTTCCTAACTGTGTTGGCTCAGGCCTTGGTCTCAAGGCCTCAAGGGCTGAATGGGGCAGGAGGGCCAGGAGCCCAAGTACTTTGAATGTGGGCCGTGG
2401 AAGCCACATAACCAGGCGGCACTAAGGGCCTTCCTAACTGTGTTGGCTCAGGCCTTGGTCTCAAGGCCTCAAGGGCTGAATGGGGCAGGAGGGCCAAGTACTTTGAATGTGGGCCGTGG
                                                                             *poly(A) site
```

*FIG. 1B*

Ha2 gene

```
                                                                        splice site #
    -120  AAGGAGAAACAATTATGTATTTTAAACCAATGTTTATATTATGTTTGTTAATTTATTCTATTCCTGCAGGTTTAAATGTTTATTTGCTACTTGGCTACTTGATTAGAGAACGCAAA 1  ATGAATAACTCAACAAACTCCCTAACAATAGCCTGGCTCTTACAAGTCCTTATAGACATTTGAAGTGGTGTTTATTGTCCTGGTGGCTGGATCCCTCAGTTTGGTGACCATTATCGGG
       1  METAsnAsnSerThrAsnSerAsnSerLeuAlaLeuThrSerProTyrLysThrPheGluValValPheIleValLeuValAlaGlySerLeuValThrIleIleGly 121  AACATCCTAGTGCTTCATGGTTTCCATTAAAGTCAACCGCCACCTCCAGACGTCAACAATTACTTTTATTCAGCTGGCTGTCTGTGCTTATCAGCTTATCATAGGTGTTTTCTCATGAACTTGTAC
      41  AsnIleLeuValMETValSerIleLysValAsnArgHisLeuValAsnAsnTyrPheLeuPheSerLeuAlaCysAlaAspLeuIleIleGlyValPheSerMETAsnLeuTyr 241  ACCCTCTACACTGTGATTGGTTACTGGCCTTTGGGACCTGTGGTTGTGACCTTTGGCTGGTCAGCAATGCCTCAGTTATGAATCTGCTCATCATCAGCTTTGAC
      81  ThrLeuTyrThrValIleGlyTyrTrpProLeuGlyProValValCysAspLeuAlaLeuAspTyrValValSerAsnAlaSerValMETAsnLeuLeuIleIleSerPheAsp 361  AGGTACTTCTGTGTCACAAAACCTCGACTTGCCTACCCAGTCAAGCGGACCACCAAAATGCCAGGTATGATGATTCAGCTGCCTGGGTCCTCTCTTCTCCTGGCTCCAGCCATTCTC
     121  ArgTyrPheCysValThrLysProLeuThrTyrProValLysArgThrThrLysMETALaGlyMETMETIleAlaAlaAlaTrpValLeuSerPheIleLeuTrpAlaProAlaIleLeu 481  TTCTGGCAGTTCATTGTAGGGGTGAGAACTGTGGAGGATGGGAGTGCTACATTCAGTTTTTTCCAATGCTATTTGGTACGGCTATTGCAGCCTTCTATTGCCAGTGATC
     161  PheTrpGlnPheIleValGlyValArgThrValGluAspGlyGlyCysTyrIleGlnPhePheSerAsnAlaValThrPheGlyThrAlaIleAlaAlaPheTyrLeuProValIle 601  ATCATGACTGTGCTATATTGGCACATATCCCGAGCCAGAAGGACAGGATAAAGAAGGACAAGAAGGAGCCCTGTTGCCAACCAAGACCCCGTTTCTCCAAGTCTGTACAAGGAAGGATA
     201  IleMETThrValLeuTyrTrpHisIleSerArgAlaSerLysSerArgIleLysLysAspLysLysGluProValAlaAsnGlnAsnGluAspProSerLeuValGlnGlyArgIle 721  GTGAAGCCAAACAATAACAACATGCCCAGCAGTGACGATGCCTGGAGCCACAACAAAATCCAGAATGGCACAAAAGGAGATCCTGTGACTGAAAACTGTGTTCAGGGAGAGGAGAAG
     241  ValLysProAsnAsnAsnAsnMETProSerSerAspAspAlaTrpSerHisAsnLysIleGlnAsnGlyLeuGluHisAlaProArgAspProValThrGluAsnCysValGlnGlyGluGluLys 841  GAGAGCTCAATGACTTCCACCTCAGTGCTGTTGCCTCAATATGAGAATGATGAAATAACCAGGATGAAAACAGTTTCCACTTCCCTGGCCATTCCAAAGATGAGAACTCT
     281  GluSerSerAsnAspSerThrSerValSerAlaValAlaSerAsnMETArgAspAspMETIleThrArgMETLysAsnValSerThrSerLeuGlyHisSerLysAspGluAsnSer 961  AAGCAAACATGCACAGAATTGCACCAAGACCCCAAAAAGTGACTTCATGTACCCAACTATACCACCGTGGAGGTAGTGGGGTCTTCAGGTCAGAATGGAGATGAAAAGCAGAATATT
     321  LysGlnThrCysIleArgIleGlyThrLysThrLysProLysSerAspSerCysThrProThrAsnThrThrValGluValGlySerSerGlyValValGlyAspGluLysGlnAsnIle 1081  GTAGCCCGCAAGATTGTGAAGATGACTAAGCACCTGCAAAAAGAAGGAGCCTCCTCCTTCCCGGAAAAGAAAGTCACCAGGACAATCTTGGCTATTCTGTTGGCTTTCATCATCACTTGG
     361  ValAlaArgLysIleValLysMETThrLysHisLeuGlnLysGluGlyAlaSerSerPheProGluLysLysValThrArgThrIleLeuAlaIleLeuLeuAlaPheIleIleThrTrp 1201  GCCCCATACAATGTCATGGTGCTCATTAACACCTTTGTGCACCTTGCATCCCAACACTGTGTGGACAATTGGTTACTGGCTTTGTTACATCAACAGCCACTATCACCCTGCCTGCTAT
     401  AlaProTyrAsnValMETValLeuIleAsnThrPheCysAlaProCysIleProAsnThrValTrpThrIleGlyTyrThrIleAsnSerThrIleAsnProAlaCysTyr 1321  GCACTTTGCAATGCCACCTTCAAGAGACCTTTAAACACCCTTCATGTGTCATTATAGAACATAGGCGCTACAAGGTAAAATATCTTTGAAAAAGATAGAAGGTGGGCAAGGGAGGCT
     441  AlaLeuCysAsnAlaThrPheLysHisLeuMETCysHisTyrLysAsnIleGlyAlaThrArg
```

FIG. 2A

```
1441  TGAGAAGAATAAAGGGATAAACGAGCTCCTAGTTTTAAAATCTCTGCCATTGCACTTTATAGTCTGATTACAAAACGTGCAATTCAGGAGCCCAGCAGTGACACACTTATCACGCCTAG
1561  GCTCCAGTTGCAAAAATTGCACCTTATAAACTGTCAGTATTAGGAGCAATGAGACAATGTTGGGATCGTGGATTTAAGAAACTATACACTGTTTCTCATAATCTCTTG
1681  AAGAAGGGCTTCTGATTCTACAATTTTATCAGTCTCTGCACAAGAGAATAACCTTGTTCCTTTTGTTACTTTGTTGTTTGTTCTCATGTGTCCTTAAGAGAAGAATGCCACAG
1801  TTACAAGGTAAACATGGAGACTTAAACATAAAGAAAATAGGCACTATACAATGGGACATAAAGAAATGAAAGAAGATGCAGAAATTTGTCTCCGAGTGTTAAGCATATTTTAT
1921  TCTTTTGTTACGGTCCTATTTAGAGGATTGGAATGTAATAAATGCTTATTTTTTGCCTTCTTTTCCACCATGAAGAGAAGAAAGCAAACAAACAGA
                                                                                           #poly(A) site
```

```
1321  CTCTGCTACGTCAACAGCACCATCAACCCTGCCTGCTGTGCAACGGCCACCTTCCGGCACCTGCTGTGCCAGTATCGGAACATCGGCACTGCCAGTAG
 441       LeuCysTyrValAsnSerThrIleAsnProAlaCysTyrAlaLeuCysAsnAlaThrPheLysLysThrPheArgHisLeuLeuLeuCysGlnTyrArgAsnIleGlyThrAlaArg

1441  GCAGGCAGGAGTGCCCTAGGAGTGCTCGTGTTGCTGCGTGCTGGGGGACCACACGGCTCACTTGCTGCGTTCAGGCACCATTCTGCGTTCACGTTTGCTGAGGAGG
1561  AAGTTCAGAAGAGGCTCTGTGCTGCATTCAGAGACCAGATCTCTGCTCAGGAGGCTCACCCCAGGAGTGTCTGAACTGGGCTGCCTGCCTCTGTGCCACCTCTGCCCTGCA
1681  GCGAGCTGCGGGGCACTGGGCCTGGGTGGGCCACTGCCCACTGTGACCAACCATCAGCAGTGCTGGAAGAATGAGAGATCTGATGGGGCCGAAGCCCAGGCCCCTCAGGAAGAACAAA
```

```
TATTGGTTGTGCTATGTCAATAGCACTGTCAACCCCATCTGCTATGCCCTCTGCAACAGAGACCCTTCAGGAAGAGACCCTTAAGATGCTGCTTCTCTGCCGATGGAAAAGAAAAAGTGGAA   1560
TyrTrpLeuCysTyrValAsnSerThrValAsnProIleCysTyrAlaLeuCysTyrAsnArgThrPheArgLysThrPheLysMetLeuLeuLeuCysArgTrpLysLysLysValGlu    520
GAGAAGTTGTACTGGCAGGGAACAGCAAGCTACCCTGAAAGTCAACACTCCTCTCGAAAGAACAATGACCACCACAGTCAACATCCTCTGAGGATGAGCAAGCTGATTCTGGTTTGTATA    1680
GluLysLeuTyrTrpGlnGlyAsnSerLysLeuPro                                                                                      532
TTTTCAAAAGAAGACATCTCATTTTGAGTCCTTGAAGATTTTTGTAAAGGCTCAAGTTTGGTTGCCAAATGGAAGGGGCCATAGCTGCAGCAATTGCTGACATATTAAATGACTCTTGC    1800
CTATGACCAAGGCCATTTGATGCCAGGGAGTTTGCCAATGAAGTAAAGGGATAAGAAGAAGACACTGGGTAACAATGAAACAGTGACTCAGGGAACTTATG                      1920
CCCCTTCTGTAGGAAACAGCAGAGACCAGGTGGAAACCTTTTCCCTGTGAAACCTGTCATAGAATTTTGTGCAATATGTATGTGTCTATGAAG                              2013
```

*FIG. 5B*

CLONED HUMAN GENES FOR MUSCARINIC ACETYLCHOLINE RECEPTORS AND CELLS LINES EXPRESSING SAME

This application is a continuation of application Ser. No. 07/944,747 filed on Sep. 14, 1992, now abandoned, which is a continuation, of application Ser. No. 07/581,538 filed on Sep. 12, 1990, now abandoned which is a continuation, of application Ser. No. 07/241,971 filed Sep. 8, 1988, now abandoned.

TECHNICAL FIELD

The present invention is related to the cloning of human genes for a plurality of different muscarinic acetylcholine receptors and providing a group of cell lines each of which individually expresses only a single, selected human muscarinic receptor.

BACKGROUND OF THE INVENTION

Cloning of certain muscarinic acetylcholine receptor genes and transient expression of the same have been reported (Peralta et al, 1987, Science 236:600–605, Bonner et al, 1987, Science 237:527–532 and Peralta et al, 1987, EMBO Journal 6:3923–3929). However, permanently stable cell lines, each of which homogeneously expresses a particular subtype of the human muscarinic acetylcholine receptor to the exclusion of the other subtypes, have not heretofore been known or described.

SUMMARY OF THE INVENTION

It is, therefore, an object of the present invention to provide a plurality of clones, each clone containing complete coding sequence for the expression of a particular, single subtype of human muscarinic acetylcholine receptor (MAR).

It is a further object of the present invention to provide a cell line for stable and homogeneous expression of a single, specific, human MAR.

It is another object of the present invention to provide a method for determining the pharmacology and the screening of muscarinic drugs intended for human use.

It is an additional object of the present invention to provide diagnostic probes for determining the level of specific subtype of MAR in human tissues or cells.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 1A and 1B shows the sequence of the human m1 receptor gene in the vicinity of the coding exon. The DNA sequence is numbered from the first nucleotide of the coding sequence. The amino acid sequence encoded by the coding sequence is shown directly below the DNA sequence. The splice acceptor site defining the 5' end of the coding exon is indicated above the sequence with the asterisk above base −79 indicating the last nucleotide of the preceding intron. The poly(A) addition site is identified by an asterisk below base 2420. The BamH I site used in construction of the expression clone is indicated at nucleotides −284 to −279.

FIGS. 2A and 2B shows the sequence of the human m2 receptor gene in the same format as described for FIGS. 1A and 1B. The splice acceptor site defining the 5' end of the coding exon is indicated above the sequence with the asterisk above base −47 indicating the last nucleotide of the preceding intron. The poly(A) addition site is identified by an asterisk below base 1976.

Figure 3A:
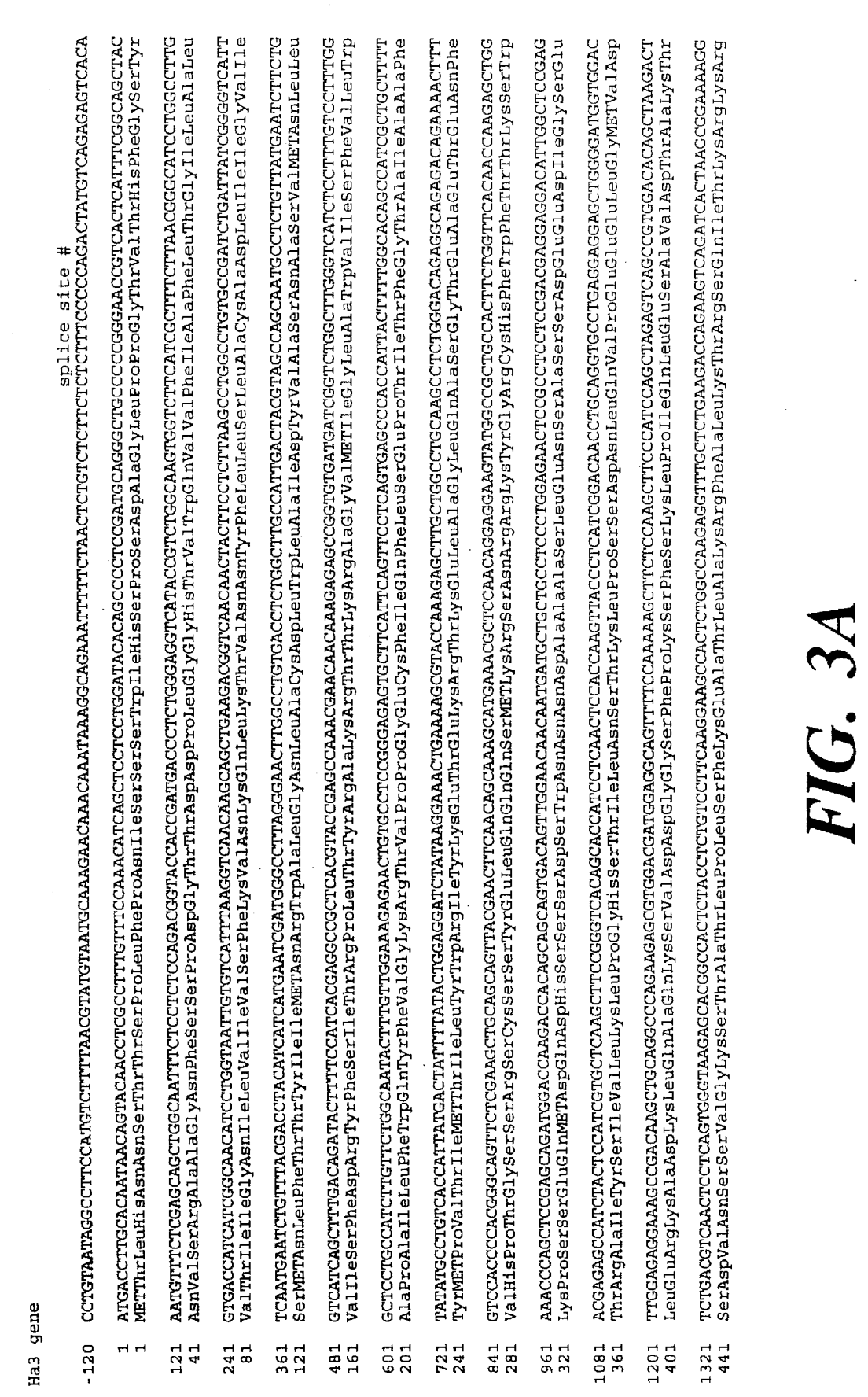
Figure 3B:
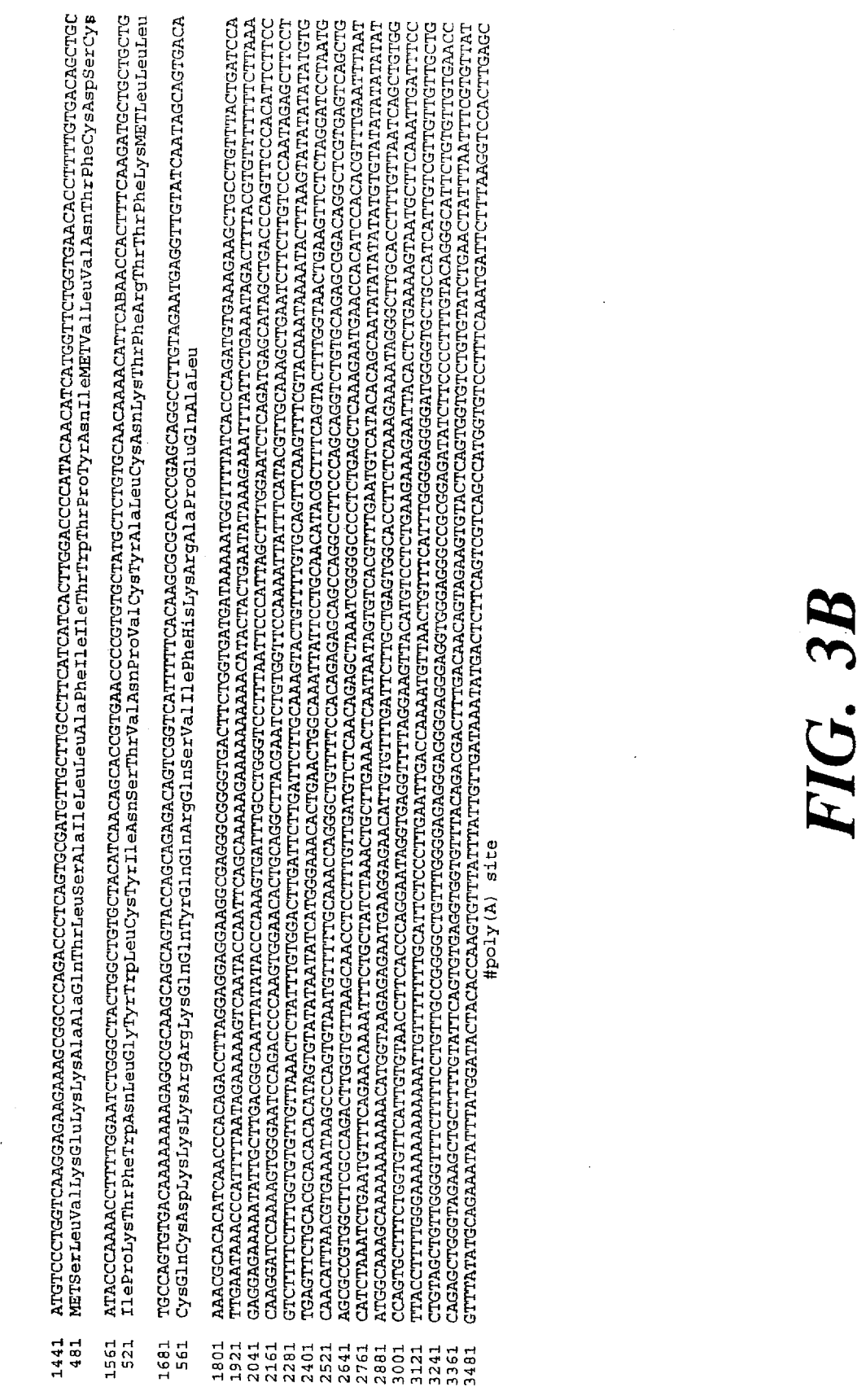

FIGS. 3A and 3B shows the sequence of the human m3 receptor gene in the same format as FIGS. 1A and 1B. The splice acceptor site is indicated with the asterisk above base −20. The poly(A) addition site is identified by an asterisk below base 3513.

Figure 4A:
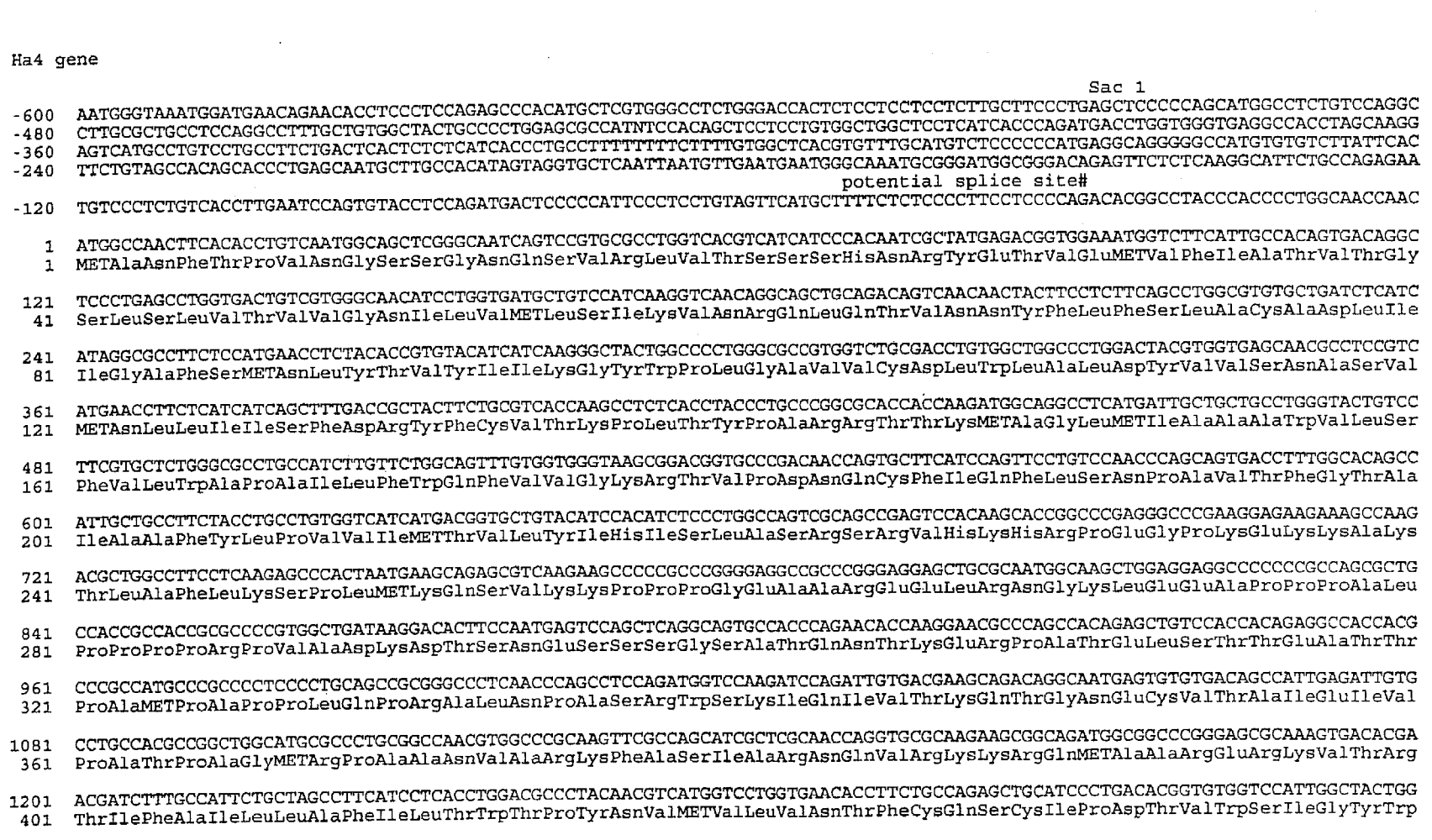

FIGS. 4A and 4B shows the sequence of the human m4 receptor gene in the same format as FIGS. 1A and 1B. The splice acceptor site is indicated by an asterisk above base −30. The sequence does not extend as far 3' as the poly(A) addition site. The Sac I site used in construction of the expression clone is indicated at nucleotides −511 to −506.

Figure 5A:
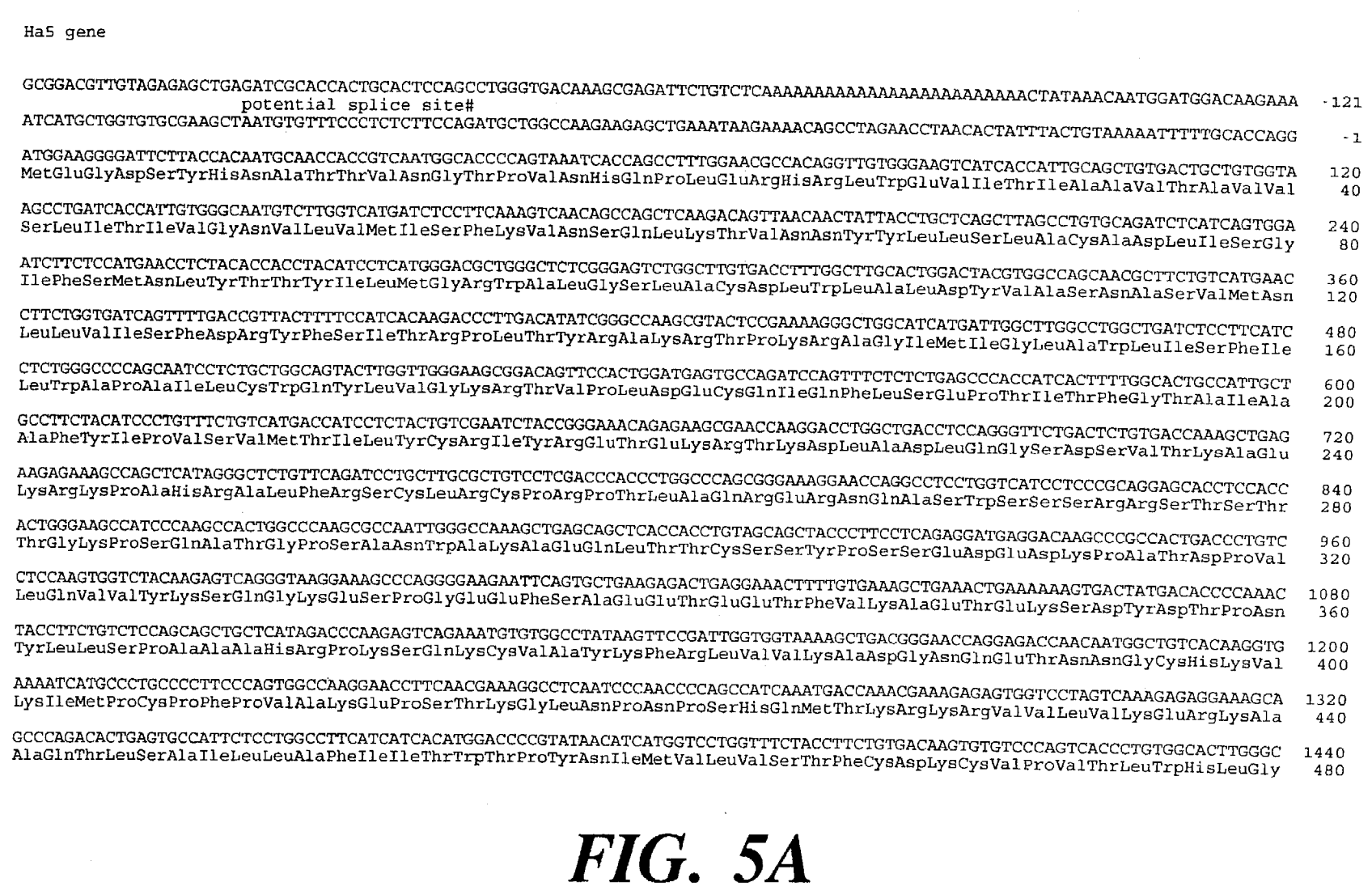

FIGS. 5A and 5B shows the sequence of the human m5 receptor gene in the same format as FIGS. 1A and 1B. The splice acceptor site is indicated by an asterisk above base −78. The sequence does not extend as far 3' as the poly(A) addition site.

DETAILED DESCRIPTION OF THE INVENTION

The above and various other objects and advantages of the present invention are achieved by cell lines which stably and homogeneously express a single subtype of human MAR at the exclusion of any other subtype of human MAR. Clones of human genes for five different MARs are also provided.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Cloning

The genes were cloned as follows. A rat cerebral cortex cDNA library (obtained from Dr. M. J. Brownstein of NIH) of 7×10$^6$ clones in the pcD mammalian expression vector (Okayama et al, Mol. Cell. Biol. 3,280–289, 1983) was screened by hybridization to an oligonucleotide probe (3'-TC TGT CAG TTG TTG ATG AAG GAC GAC TCG GAC CGG ACA CGA CTG GAG TAG TAC CCG-5'). This probe was based on nucleotides 170–225 of the noncoding strand of the porcine brain (m1) cDNA (Kubo et al, 1986, Nature, 323:411) but modified at positions 5, 38, and 53 to more accurately reflect mammalian codon usage and to better approximate the hamster $\beta_2$-adrenergic receptor sequence from which it differs by 14 bases. Using a combination of standard techniques, cDNA clones were identified by hybridization to Southern blots made from Bam HI or Xho I digests of plasmid DNA from twelve different cultures containing pools of as many as 5×10$^5$ independent clones. Cultures containing hybridizing bands of interest were used to seed twelve new cultures each containing ten-fold fewer clones, the cultures were grown to amplify the new pools, and the process repeated until a pool containing less than 5×10$^3$ independent clones and containing only a single hybridizing band was identified. At this point the pool of clones was plated and the clone isolated by colony hybridization. The blots and colony filters were hybridized in 6x standard saline citrate (SSC) (0.9M NaCl, 0.09M sodium citrate, pH 7.0) at 60° C. to the oligonucleotide that had been labeled with $^{32}P$ by using T4 polynucleotide kinase. Filters were washed under the same conditions as hybridized. Three cDNAs were identified as Bam HI and Xho I bands of the following sizes (in kilobases): m1, 1.8 and 2.9; m3, 2.8 and 3.9; and m4, 2.4 and 1.05. These cDNAs were sequenced and clearly encoded three different but related proteins. The m4 cDNA lacks the first five bases of the coding sequence as determined by comparison with the human m4 gene described herein infra.

Figure 1A:
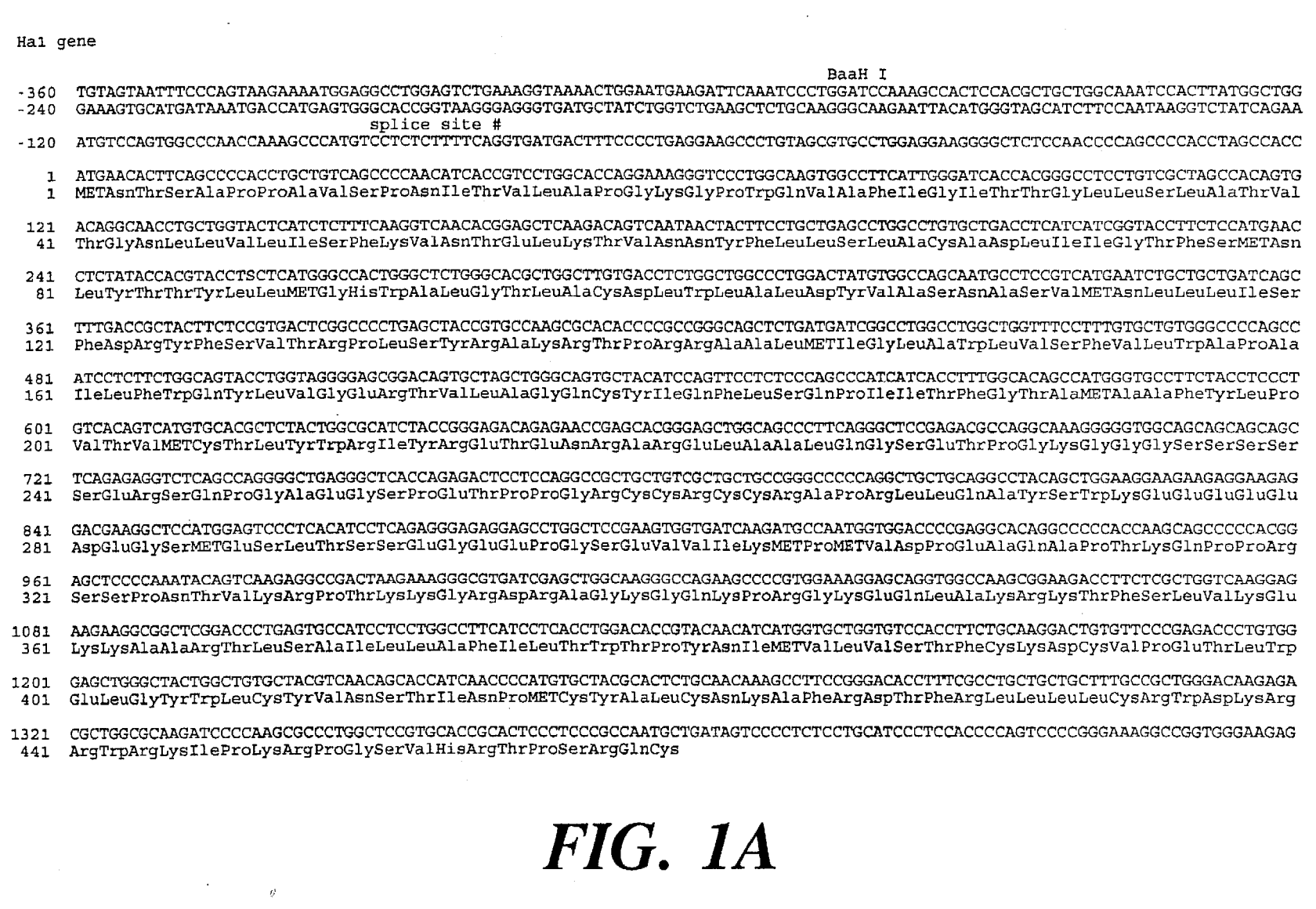

The 0.51 kb Sac I-Pst I fragment corresponding to amino acids 55 to 224 of the m1 cDNA was cloned into the pSP64 plasmid (obtained from Promega, Madison, Wis.) to make clone cRm1p5 which was used as a nick-translated probe to screen a partial Hae III-Alu I human genomic library (Lawn et al, *Cell* 15, 1157, 1978) by hybridization in 3× SSC at 60° C. In this manner clones representing five different human genes, m1, m2, m3, m4, and m5 were obtained and sequenced in the region of the exon which contains the complete coding sequence as shown in FIGS. 1A though 5B.

Expression vectors

The vector for expressing human m1 receptor contains a 1.8 kb Bam HI-BstE II fragment from the human gene which contains 208 nucleotides of intron sequence preceding the coding exon and 1.6 kb of the 5' end of the coding exon (including the full coding sequence) substituted for the 1.8 kb Bam HI-BstE II fragment of the rat m1 cDNA clone.

A hybrid DNA containing human m2 gene coding sequence and rat m4 cDNA 3' untranslated sequences was created for expression of the human m2 receptor. The 5' end of the human sequence is defined by a Dra I site (−43, numbering from the A of the initiation codon) and the 3' end by an Avr II site (1556 to 1561) in the 3' untranslated region. The 5' end was ligated to the pcD vector at the Pst I site which normally defines the 5' end of a cDNA using a Pst I-Hinc II linker from pUC18. The Avr II site was ligated to the Avr II site of the rat m4 cDNA so that most of the 3' untranslated sequence and the poly(A) tail are derived from the m4 cDNA.

For expression of the m3 and m5 receptors in mammalian cells, use was made of pCD-PS, a modified form of the pCD vector which was derived from the rat m1 cDNA clone by replacing all but the last few bases of the cDNA with a linker (CTGCAG CCCGGG AGATCT GGTACC GAGCTC GAATTC ACTAGT) containing Pst I, Sma I, Bgl II, Kpn I, Sac I, Eco RI, and Spe I sites. Except for the Pst I site which corresponds to the site at which the G-tailed 5' end of a cDNA is normally inserted into the pCD vector, all of the sites in the linker do not occur elsewhere in the vector. The Spe I site is followed by GGG and about 40 bases of the A tail derived from the m1 cDNA.A2.74 kb TthIII-SacI fragment of the human m3 gene containing 16 bases of 5' untranslated sequence, the complete coding sequence, and 952 bases of 3' untranslated sequence was inserted into the SmaI and SacI sites of pCD-PS after filling the TthIII sticky end using Klenow fragment of *E. coli* DNA polymerase.

For expression of the human m4 receptor, human m4 5' untranslated and coding sequence was substituted for the rat coding sequence of the m4 cDNA clone, thereby making a hybrid DNA containing human coding and rat 3' untranslated sequences. The two sequences were joined at an Avr II restriction site that occurs at the beginning of the 3' untranslated sequence of both clones. Because there was no convenient restriction site in the 30 bases between the initiation codon and the possible splice acceptor site with which to join the coding sequence to the SV40 promoter, a Sac I site located 506 to 511 base upstream was used and ligated to the Bam HI site in the SV40 intron of the pcD vector, using the Bam HI-Sac I portion of the pUC 18 multiple cloning site as a linker. This construct removes the 19S splice acceptor as well as the SV40 19S initiation codon, forcing the use of an initiation codon in the human sequence and the putative human splice acceptor site.

For expression of the human m5 receptor, the pCD-PS vector was used. The Bal I (nucleotide-70) to Pst I (nucleotide 1774) portion of the gene was inserted into the Sma I and Kpn I sites of the pCD-PS vector using a Pst I-Kpn I linker derived from pUC18 to create the plasmid Hm5pCDp1. A second construct, Hm5pCDp2, containing the same Bal-Pst portion of the human clones but combined with the last 1 kb of the 3' untranslated sequence of the rat m4 cDNA was created by removing the 2.4 kb HindIII-KpnI fragment from Hm5pCDp1 and inserting it into the 3.6 kb Hind-Kpn fragment of the m4 cDNA which contains most of the pCD vector and the poly(A)-containing portion of the 3' untranslated sequence.

The plasmids thus prepared, such as Hm5pCDp2, were used for transfections to establish stable cell lines.

Transfection and Establishment of Cell Lines

Chinese hamster ovary cells (CHO-K1) were transfected using the modified calcium phosphate procedure (Chen et al. Molec. and Cell Biology 7:2745–2752, 1987). Cells were seeded into six well plates at a density of $10^5$ cells/well in growth medium consisting of Minimum Eagle's, Medium supplemented with 10% fetal calf serum (Gibco) and 1000 U each of penicillin G and streptomycin and 4 mM glutamine (Whitaker M.A Bioproducts). Except for the overnight (10–16 hours) transfection (see below) cells were incubated in a humidified incubator at 37° C. and 5% $CO_2$. 24 hours later, 4 µg of pCD vector containing a muscarinic receptor cDNA and 0.4 µg of pCDneo, a plasmid conferring neomycin resistance (Chen et al, supra) were mixed with 200 µl of 0.1M $CaCl_2$ and 200 µl of 2×BBS [50mM N-, N-Bis(2-hydroxyethyl)-2-aminoethanesulfonic acid (BES), pH 6.89 containing 280 mM NaCl and 1.5 mM $Na_2HPO_4$] at room temperature (22°–25° C.) for 10 minutes before adding to one well containing 2 ml of growth medium. Cells were transferred to a humidified incubator at 35° C. and 3% $CO_2$ and incubated overnight (10–16 hours). The following day cells were washed and given fresh medium. 24 hours later cells were trypsinised and split at a ratio of 1:20 into four 10 cm plates. The next day selection medium, growth medium containing 400 µg/ml of the neomycin analog G418 (Gibco), was added and selection continued for 2–3 weeks with selection medium being changed every three days. At the end of selection, transfected cells were harvested and plated at limiting dilution into 96-well plates. Single colonies were selected, expanded and tested for the presence of muscarinic receptors by binding of $^3H$-NMS (N-methylscopolamine).

It should be noted that techniques similar to the above-described methodologies can be easily adapted and employed by one of ordinary skill in the art to produce other cloning or expression vectors using different promoters and to transfect other cell lines which allow, for instance, coupling to different cellular responses than those obtainable with CHO cell line.

Binding Assays

Transfected cells were grown to confluence, washed and scraped into cold binding buffer and homogenized for 30 seconds in a Tekmar Tissumizer (setting 50). Membranes were pelleted at 14,000 g, rehomogenized and the membrane protein determined using a Biorad Protein assay dye reagent. Membrane concentration was adjusted to 1mg protein/ml and stored frozen at −80° C. prior to use.

All membranes, drugs and radioligands were made up in binding buffer which consisted of 25 mM sodium phosphate (pH 7.4) containing 5 mM magnesium chloride. Assays were conducted in 1 ml total volume. Final membrane protein concentrations were 30 ug/ml (m1), 70 ug/ml (m2), 4 µg/ml (m3), 7 µg/ml (m4), and 3 µg/ml (m5). For direct binding assays, $^3$H-NMS concentrations between 2.5 pM and 300 pM were used. For inhibition experiments either 150 pM or 300 pM $^3$H-NMS was used. Incubations were initiated by addition of $^3$H-NMS and carried out at 22° C. for 3 hours. Displaceable binding was assessed in the presence of 1 uM atropine sulphate. Binding was terminated by filtration through a Brandel cell harvester onto Whatman GF/C filters. Membranes were washed three times with ice-cold binding buffer before drying, transferring to 10 ml scintillant (NEN Aquasol) and counting in an LKB 1217 Beta counter.

Utility of the Invention

The cell lines described herein, as well as other cell lines produced in a similar manner using different host cells and the same or similar expression vectors, have their primary utility in screening for drugs with improved specificity for an individual receptor type. Their utility in defining the properties of antagonists, i.e., drugs which block the receptors, is illustrated in Table 1. The binding properties of antagonists are defined mainly by the structure of the receptor protein and would not be expected to depend on the levels of the receptor expressed per cell or on other constituents of the cell. On the other hand the binding properties of agonists, i.e., drugs which stimulate the receptors, is highly dependent on the levels of receptor relative to the GTP-binding proteins with which the receptor couples to induce a functional response in the cells. It has been determined that the m1–m5 m receptors are at least able to couple with GTP-binding proteins in the CHO cells, and these receptors induce functional responses when stimulated by agonists (data not shown). The functional responses observed for one or more of the receptors include stimulation of phosphatidylinositol hydrolysis and arachidonic acid release, increases or decreases in cyclic AMP levels, and reduction of mitogenesis. Any of these responses could form the basis of a functional assay for the screening of muscarinic agonists with these or similar cell lines. The functional responses can be determined by any standard procedure.

The amino acid sequences and the expression vectors described herein also allow rational drug design. This is accomplished in part by identifying the differences between the receptors as provided by the amino acid sequences and by identifying the specific sites important for the binding of the drug to the receptor. Expression of high levels of the individual receptors may allow purification of enough of the individual proteins to allow biophysical determination of their three dimensional structure. Additionally, the present expression vectors can be altered by well established techniques of site-directed mutagenesis to produce altered protein sequences when transfected into CHO or other cells. Analysis of such mutated receptors by standard methodology could identify the amino acids which form the ligand or drug binding sites, allowing better design of putative drugs.

Furthermore, the DNA sequences described herein allow the independent isolation of the MAR genes, confirmation of the identity of cloned cDNAs of MAR and the synthesis of probes to be used for hybridization to mRNA or for diagnostic purposes. These are accomplished by standard techniques well known in the art.

Moreover, the amino acid sequences of the receptor proteins allow the synthesis of peptides which can be used as antigens to raise antibodies having specific binding affinity for a particular receptor subtype. Of course, these antibodies can be employed to more clearly define the localization of the receptor types than is possible using in situ hybridization to mRNA and for diagnostic purposes if clinically significant abnormalities are found in any of the receptor subtypes. It is pointed out that the methodologies for the various utility mentioned herein are standard techniques quite conventional and well known to one of ordinary skill in the art and such methodologies are not a part of this invention.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Binding parameters for binding of muscarinic antagonists to cloned muscarinic receptors expressed in CHO cells

| | Antagonist | | | | | |
|---|---|---|---|---|---|---|
| | $^3$H-NMS | | AF-DX 116 | | Pirenzepine | |
| Receptor | $K_D$ (pM) | $B_{max}$ (fmol/mg protein) | $IC_{50}$ (µM) | $K_i$ (µM) | $IC_{50}$ (nM) | $K_i$ (nM) |
| Rm1 | 65 ± 8 | 180 ± 43 | 4.3 ± 1.2 | 1.3 | 89 ± 16 | 17 |
| Hm2 | 422 ± 113 | 121 ± 63 | 0.36 ± 0.23 | 0.26 | 1541 ± 99 | 794 |
| Hm3 | 55 ± 8 | 1981 ± 423 | 3.1 ± 0.4 | 0.82 | 1171 ± 149 | 182 |
| Hm4 | 49 ± 10 | 903 ± 241 | 1.8 ± 0.3 | 0.45 | 561 ± 73 | 87 |
| Hm5 | 106 ± 7 | 2236 ± 590 | 6.8 ± 0.9 | 2.8 | 390 ± 52 | 102 |

Data from two to four experiments were independently fit by nonlinear regression to a single mass-action binding site. The average values of the parameters derived from the fits and their standard errors are presented. When the data were alternatively fit to a single mass action binding site with a variable Hill number, the average Hill numbers did not vary significantly from unity except for m4(NMS), m5(pirenzepine), m4(AF-DX 116), and m4(pirenzepine) which respectively gave H=0.75±0.05, 0.84±0.01, 0.79±0.03, and 0.75±0.05. Note Rm1 is the rat m1 receptor, not the human m1 receptor.

What is claimed is:

1. An isolated DNA molecule encoding the amino acid sequence of human m5 subtype muscarinic acetylcholine receptor shown in FIGS. 5A and 5B.

2. The isolated DNA molecule of claim 1 comprising the nucleotide sequence shown in FIGS. 5A and 5B.

3. A cell line consisting of mammalian cells which are transfected with and stably express the DNA of claim 2 such that human m5 subtype muscarinic acetylcholine receptor is the single muscarinic acetylcholine receptor expressed by said cell.

4. A cell line consisting of mammalian cells which are transfected with and stably express the DNA of claim 1 such that human m5 subtype muscarinic acetylchline receptor is the single muscarinic acetylchline receptor expressed by said cell.

5. The isolated DNA of claim 1 which is a vector.

6. The isolated DNA of claim 2 which is a vector.

7. The vector of claim 5 which further comprises DNA elements for expression of the m5 muscarinic receptor in a mammalian cell.

8. The vector of claim 6 which further comprises DNA elements for expression of the m5 muscarinic receptor in a mammalian cell.

* * * * *